United States Patent
Joshi et al.

(10) Patent No.: US 12,295,958 B2
(45) Date of Patent: May 13, 2025

(54) READY-TO-USE INJECTABLE FORMULATIONS

(71) Applicant: Zoetis Services LLC, Parsippany, NJ (US)

(72) Inventors: Vijaya Bharti Joshi, Portage, MI (US); Laibin Luo, Kalamazoo, MI (US); Todd P. Foster, Kalamazoo, MI (US)

(73) Assignee: Zoetis Services LLC, Parsippany, NJ (US)

( * ) Notice: Subject to any disclaimer, the term of this patent is extended or adjusted under 35 U.S.C. 154(b) by 805 days.

(21) Appl. No.: 17/435,429

(22) PCT Filed: Mar. 5, 2020

(86) PCT No.: PCT/US2020/021060
§ 371 (c)(1),
(2) Date: Sep. 1, 2021

(87) PCT Pub. No.: WO2020/181024
PCT Pub. Date: Sep. 10, 2020

(65) Prior Publication Data
US 2022/0125798 A1 Apr. 28, 2022

Related U.S. Application Data

(60) Provisional application No. 62/814,440, filed on Mar. 6, 2019.

(51) Int. Cl.
*A61K 31/546* (2006.01)
*A61K 9/00* (2006.01)
*A61K 47/14* (2017.01)

(52) U.S. Cl.
CPC .......... *A61K 31/546* (2013.01); *A61K 9/0019* (2013.01); *A61K 47/14* (2013.01)

(58) Field of Classification Search
CPC ..... A61K 47/14; A61K 9/0019; A61K 31/546
See application file for complete search history.

(56) References Cited

U.S. PATENT DOCUMENTS

| | | |
|---|---|---|
| 5,318,781 A | 6/1994 | Shah et al. |
| 2002/0110561 A1 | 8/2002 | Teagarden et al. |
| 2004/0115260 A1 | 6/2004 | Schmid et al. |
| 2004/0214753 A1 | 10/2004 | Britten et al. |
| 2010/0125060 A1 | 5/2010 | Razzak et al. |
| 2013/0309226 A1 | 11/2013 | Armstrong et al. |
| 2015/0045337 A1 | 2/2015 | Al Alawi et al. |
| 2016/0176986 A1* | 6/2016 | Armstrong ....... A61K 39/39591 424/143.1 |
| 2021/0177808 A1 | 6/2021 | Freehauf et al. |

FOREIGN PATENT DOCUMENTS

| | | |
|---|---|---|
| CN | 1517090 A | 8/2004 |
| CN | 1569000 A | 1/2005 |
| CN | 108578362 A | 9/2018 |
| GB | 1 527 638 A | 10/1978 |
| WO | 2012095438 A1 | 7/2012 |
| WO | WO 2013/095166 A1 | 6/2013 |

OTHER PUBLICATIONS

Kenneth et. al. (Journal of Pharmaceutical Sciences (1984), 73:1602-1606). (Year: 1984).*
Jain, International Journal of Pharmaceutics, 2016, vol. 514, pp. 308-313.
Wernick, M. B., "Cefovecin: a new long-acting cephalosporin," Journal of Exotic Pet Medicine, 2010, vol. 19, No. 4, pp. 317-322.
Kenneth S. E. Su, et al., "Nonaqueous Cephalosporin Suspension for Parenteral Administration: Cefazolin Sodium," Journal of Pharmaceutical Sciences, vol. 73, No. 11, Nov. 1984, pp. 1602-1606.

* cited by examiner

*Primary Examiner* — Marcos L Sznaidman
(74) *Attorney, Agent, or Firm* — Paul M. Misiak

(57) ABSTRACT

The invention describes a ready-to-use injectable cephalosporin composition with reasonable viscosity, resuspendability, and syringeability attributes for injection as an antibiotic for animals.

13 Claims, 5 Drawing Sheets

Figure 1. Viscosity Vs. Shear Rate
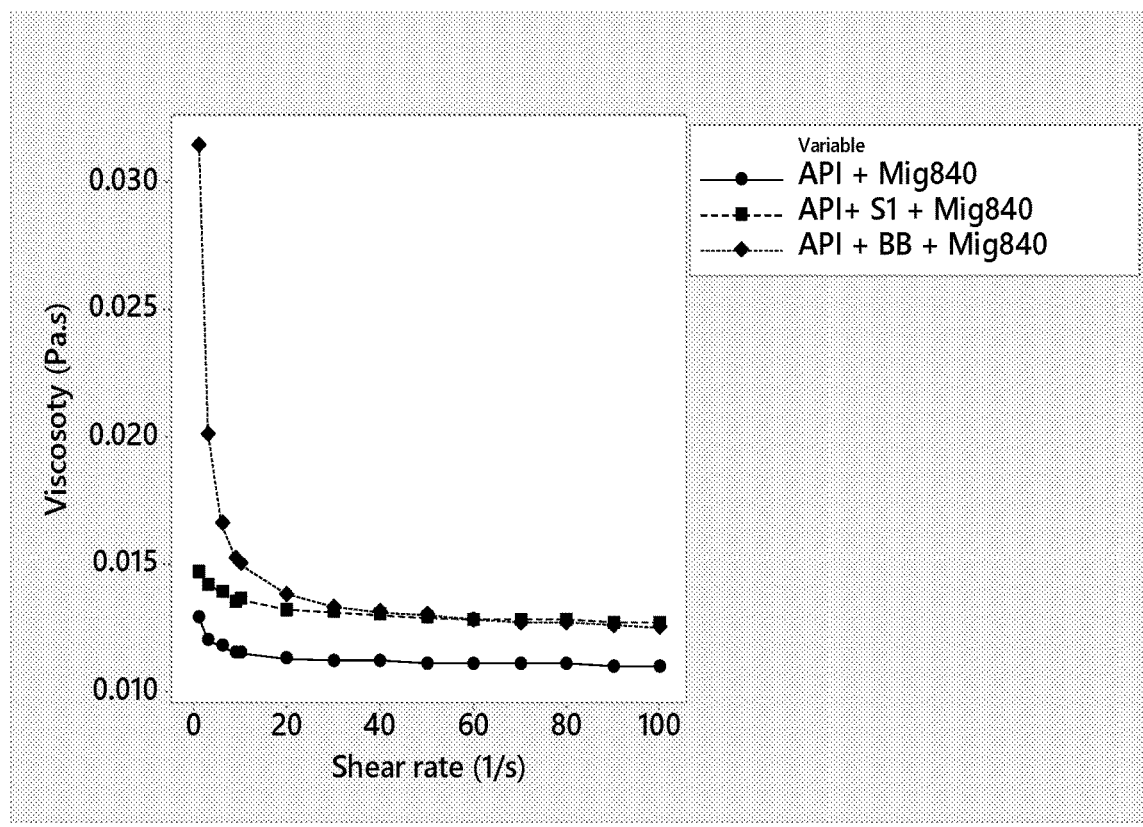

Figure 2. Viscosity vs Shear Rate with different amounts of solvent and a surfactant
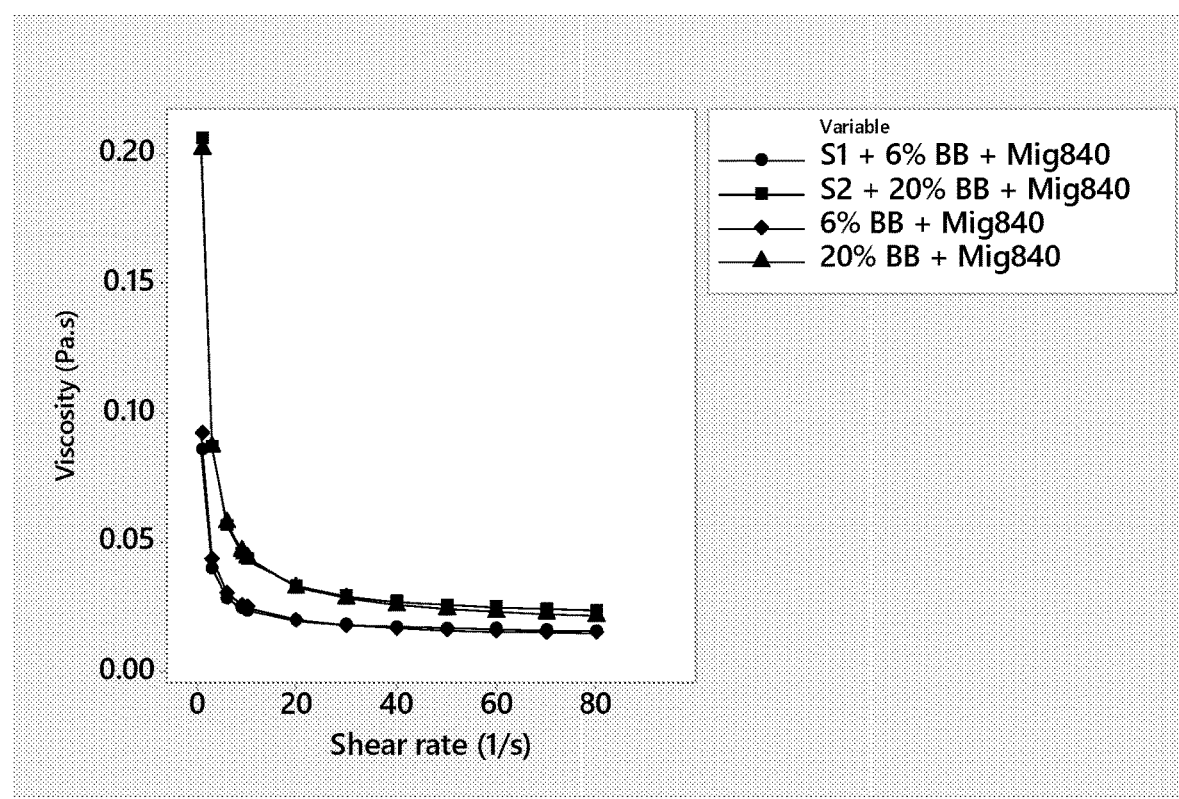

Figure 3. Viscosity versus Shear Rate with different amounts of solvent
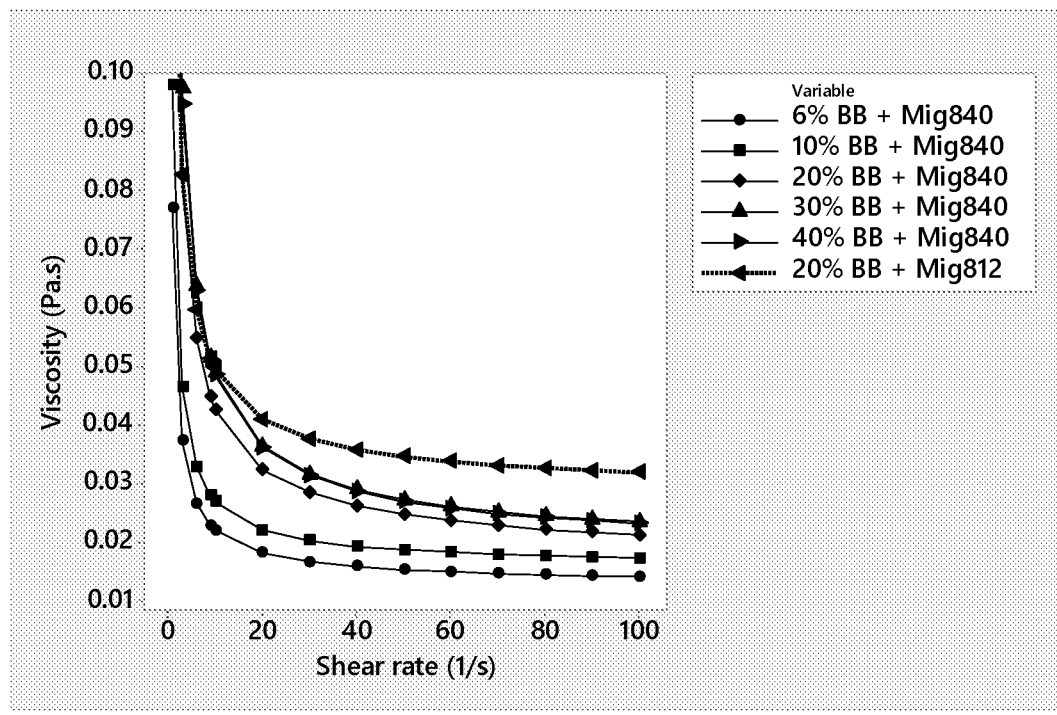

Figure 4. Syringe Force for Miglyol 812 and Miglyol 840
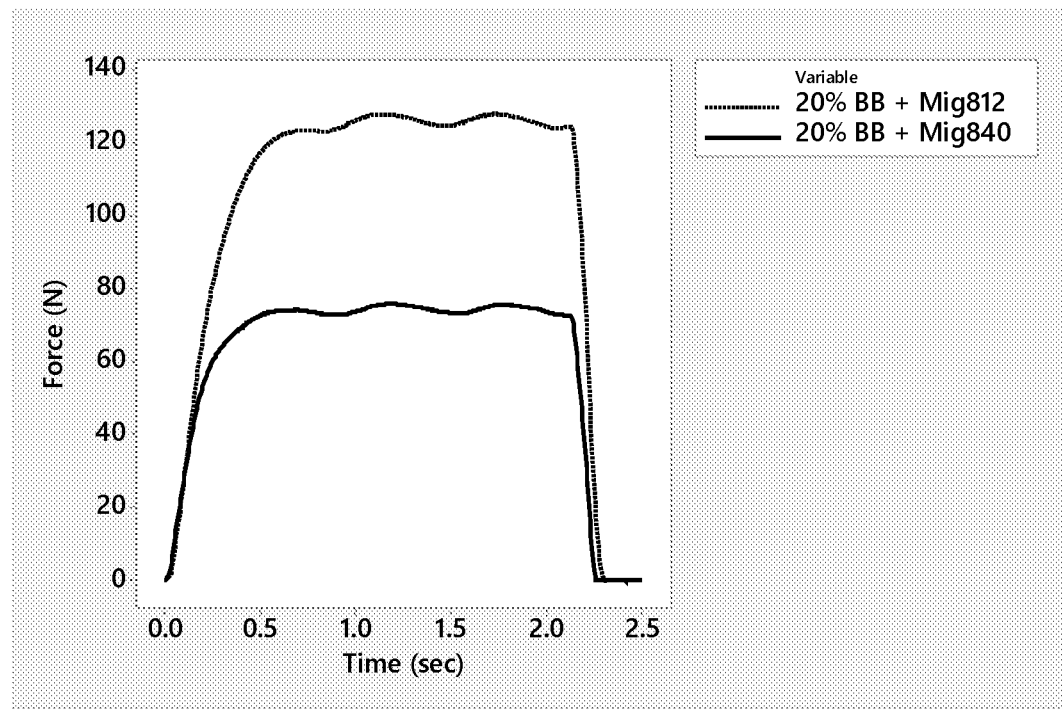

Figure 5. Resuspension Time
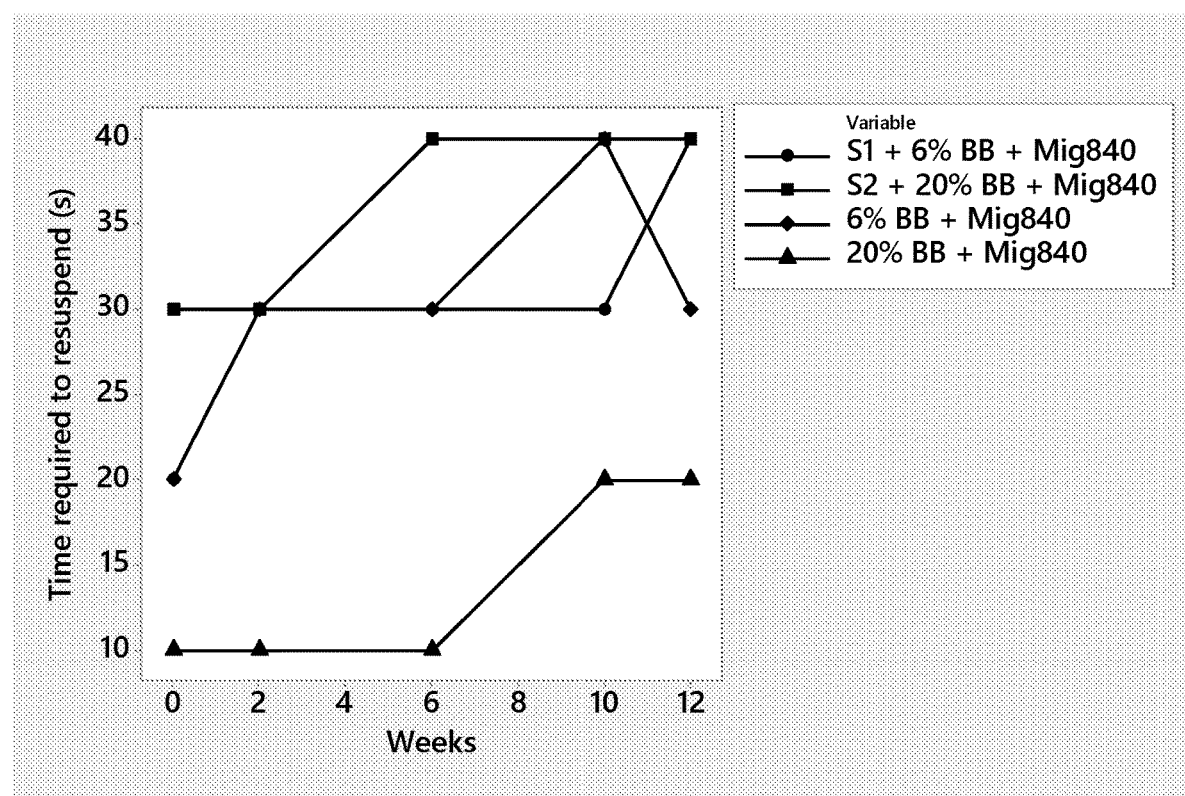

READY-TO-USE INJECTABLE FORMULATIONS

CROSS-REFERENCE TO RELATED APPLICATIONS

This application is a US National Stage entry of International Application No. PCT/US2020/021060, filed Mar. 5, 2020, which claims the benefit of U.S. Provisional Application No. 62/814,440, filed Mar. 6, 2019.

FIELD OF THE INVENTION

The present invention provides for a novel ready-to-use veterinary injectable composition comprising a class of drugs known as cephalosporins. The preferred cephalosporin drug is a third-generation cephalosporin, cefovecin sodium (Convenia®). More particularly, the present invention provides for a novel ready-to-use cefovecin sodium injectable composition that is a suspension with improved properties, for example, resuspendability, syringeability, and product ease of use.

BACKGROUND OF INVENTION

Injectable suspensions are heterogeneous systems consisting of a solid phase dispersed within a liquid phase. They must be isotonic, sterile, pyrogen free and maintain suitable physical and chemical stability over the intended shelf-life. They are limited to subcutaneous and intra-muscular routes of administration. Certain advantages of injectable suspensions include, for example, therapeutic use of drugs that are insoluble in conventional water miscible solvents, stability, depot preparations, and elimination of first-pass hepatic effects. Disadvantages of injectable suspensions include, for example, difficulty in formulation and manufacturing, syringeability, uniformity of dose, physical stability, and resuspendability. Syringeability and resuspendability depend on viscosity and particle characteristics of the active agent. According to Higuchi, et. al., Remington's Pharmaceutical Sciences, 17th Edition. 1985, p. 313; states that the major challenge with developing a good suspension is obtaining physical stability: the three major problem areas associated with suspensions are (1) adequate dispersion of the particles in the vehicle, (2) settling of the dispersed particles, and (3) caking of these particles in the sediment to resist redispersion. It is generally recognized in the art that controlled particle-to-particle interaction is a method to produce physically stable suspensions. The particle interaction must result in a loose particle aggregation so when the suspension is shaken the particles can separate to some extent to produce a uniform suspension for the administered dose. Particle attraction must be strong enough so particle aggregation occurs, however, particle aggregation cannot be too strong such that the particles will never separate. According to Stoke's Law, the rate of particle settling decreases with a decrease in particle size and particle density, and an in increase in medium (diluent) density and viscosity. Proper particle size/density and medium density and viscosity allows particles to settle with high sedimentation volumes so as not to pack tightly on the bottom of the vial or storage container, i.e., cake. Over time, the suspended particles gradually settle and may cake making it difficult to redisperse prior to use. Further, shipment of the product causes vibrational packing of the particles and/or settled cake making it even more difficult to resuspend prior to use. Resuspension of drug should occur easily with mild shaking or agitation (i.e., shear force) and result in a homogenous injectable suspension. In view of the disadvantages, injectable suspensions are one of the most difficult dosage forms to develop in terms of their stability, manufacture and usage.

In one study, (Jain, et. al., Intl. J. of Pharmaceutics, 514, (2016) 308-313, showed that flocculation and suspension caking of penethamate in oily vehicles was highly variable and depended on glass versus plastic vials, concentration dependent amounts of flocculating agent, oil, storage time, and transport vibration. Earlier in-lab syringeability and stability studies found ethyl oleate to be the best solvent as a result of penethamate solubility. Addition of 0.15% Tween 80 as a flocculating agent showed good resuspendability whereas the formulated suspension without Tween 80 required vigorous shaking and vortexing to disperse the cake. Surprisingly, addition of 0.5% Tween caused a hard cake to form. Addition of 0.5% polyethylene glycol-12-oleate prevented caking, whereas addition of a hydrophilic polymer, PVP K30, in addition with 0.5% Tween 80 did not solve the caking problem but 0.5% Span did. Addition of increasing concentrations of phospholipids (Lipoid S100) to suspensions containing PEG-12-oleate led to less dispersable sediments. The 0.15% Tween and ethyl oleate formulation was prepared in glass bottles and shipped to a clinical site. To the surprise of the investigators, the alleged stable/redispersable formulation had formed a "rock solid" cake after being transported by road and air, accounting for only about 2 hours and about 1 hour, respectively, to the test site.

The type of oil also influenced caking behavior of penethamate. For example, suspensions made in two medium chain oils, Miglyol 840 (propylene glycol dicaprylate/dicaprate) and Miglyol 812 (caprylic/capric triglyceride) were difficult to redisperse after vibration whereas the suspension prepared in a mixture of long chain saturated and unsaturated fatty acids (66% linoleic acid, 21% oleic acid, 6.4% palmitic acid, 4.0% arachidic acid, 1.3% stearic acid, and 0.8% behenic acid) dispersed readily. Addition of phospholipid to this latter formulation also led to caking on vibration. In essence, redispersability of a suspension formulation is highly unpredictable. Bauer, et. al., (GB1527638) described an oily suspension of the anthelmintic, niclosamide that purportedly provided less niclosamide crystallization and particle size growth with improved plasma concentrations. The described oils were vegetable oil, medium chain and long chain length saturated oils with surface active agents (emulsifiers and wetting agents, particularly, lecithin or polyoxyethylated sorbitan monolaurate for resorption. The examples included micronized niclosamide with liquid paraffin or sesame oil and lecithin or polyethylated sorbitan monolaurate. The niclosamide suspensions were prepare by mixing the niclosamide with a portion of liquid paraffin or sesame oil, adding glass beads and stirred at high speed with a ball mill to decrease at least 50% of the particles to less than 1µ as a mean of preventing particle crystallization and agglomeration. However, the glass beads had to be removed before use of the composition.

Besides particle size and particle surface area, it has been shown that suspension formulations vary widely and that sedimentation, caking, redispersability, and syringeability are affected by numerous factors including solvent wettability, flocculation, flocculating agent(s), net charges, solubility and stability of the active agent, solvent characteristics, oil characteristics, and others. To ensure overall stability, syringeability, and resuspendability of the active ingredient (cefovecin, sodium salt) in a ready-to-use injectable suspension, it was found that the use of benzyl benzoate in a biocompatible oil, preferably propylene glycol dicaprylate/dicaprate, provided the high viscosity and low particle settling at low shear forces; and after resuspension at high shear force had a lower viscosity for improved syringeability.

SUMMARY OF THE INVENTION

The present invention describes a ready-to-use injectable suspension composition comprising a cephalosporin in a biocompatible oil and a non-aqueous solvent that has a higher viscosity at low shear forces thereby minimizing particle settling and caking of the suspended cephalosporin and has a lower viscosity at high shear force to maximize suspendability and syringeability.

In one aspect of the invention, is a ready-to-use injectable composition comprising a cephalosporin, a biocompatible oil, and a non-aqueous solvent, wherein the composition is a suspension. In another aspect, is a ready-to-use injectable suspension composition comprising a cephalosporin, a biocompatible oil, and a non-aqueous solvent, wherein the non-aqueous solvent is benzyl benzoate. In another aspect, is a ready-to-use injectable suspension composition comprising a cephalosporin, a biocompatible oil, and a non-aqueous solvent, wherein the non-aqueous solvent is benzyl benzoate and the biocompatible oil is propylene glycol dicaprylate/dicaprate. In another aspect, is a ready-to-use injectable suspension composition comprising a cephalosporin, a biocompatible oil, and a non-aqueous solvent, wherein the cephalosporin is cefovecin, the non-aqueous solvent is benzyl benzoate and the biocompatible oil is propylene glycol dicaprylate/dicaprate. In another aspect, is a ready-to-use injectable suspension composition comprising a cephalosporin, a biocompatible oil, and a non-aqueous solvent, wherein the cephalosporin is cefovecin sodium, the non-aqueous solvent is benzyl benzoate and the biocompatible oil is propylene glycol dicaprylate/dicaprate. In another aspect, is a ready-to-use injectable suspension composition containing a cephalosporin, a biocompatible oil, and a non-aqueous solvent, wherein the cephalosporin is cefovecin sodium, the non-aqueous solvent is benzyl benzoate and the biocompatible oil is propylene glycol dicaprylate/dicaprate. In another aspect, the ready-to-use injectable suspension composition is a sterile composition that is administered by subcutaneous injection.

In another aspect of the invention, is a ready-to-use injectable suspension composition comprising a cephalosporin, a biocompatible oil, and a non-aqueous solvent, wherein the non-aqueous solvent is benzyl benzoate in the amount of about 12 w/w % to about 25 w/w % of the total weight of the composition. In another aspect, is a ready-to-use injectable suspension composition comprising a cephalosporin, a biocompatible oil, and a non-aqueous solvent, wherein the non-aqueous solvent is benzyl benzoate in the amount of about 12 w/w % to about 25 w/w % of the total weight of the composition, and the biocompatible oil is propylene glycol dicaprylate/dicaprate in the amount of about 58 w/w % to about 68 w/w % of the total weight of the composition. In another aspect, is a ready-to-use injectable suspension composition comprising a cephalosporin, a biocompatible oil, and a non-aqueous solvent, wherein the non-aqueous solvent is benzyl benzoate in the amount of about 12 w/w % to about 25 w/w % of the total weight of the composition, and the biocompatible oil is propylene glycol dicaprylate/dicaprate in the amount of about 58 w/w % to about 68 w/w % of the total weight of the composition, and the cephalosporin is cefovecin in an amount of about 120 mg/mL to about 180 mg/mL. In another aspect, is a ready-to-use injectable suspension composition containing a cephalosporin, a biocompatible oil, and a non-aqueous solvent, wherein the non-aqueous solvent is benzyl benzoate in the amount of about 12 w/w % to about 25 w/w % of the total weight of the composition, and the biocompatible oil is propylene glycol dicaprylate/dicaprate in the amount of about 58 w/w % to about 68 w/w % of the total weight of the composition, and the cephalosporin is cefovecin in an amount of about 120 mg/mL to about 180 mg/mL. In another aspect, is a ready-to-use injectable suspension composition comprising a cephalosporin, a biocompatible oil, and a non-aqueous solvent, wherein the non-aqueous solvent is benzyl benzoate in the amount of about 12 w/w % to about 25 w/w % of the total weight of the composition, and the biocompatible oil is propylene glycol dicaprylate/dicaprate in the amount of about 58 w/w % to about 68 w/w % of the total weight of the composition, and the cephalosporin is cefovecin sodium wherein cefovecin is in an amount of about 120 mg/mL to about 180 mg/mL. In another aspect, is a ready-to-use injectable suspension composition containing a cephalosporin, a biocompatible oil, and a non-aqueous solvent, wherein the non-aqueous solvent is benzyl benzoate in the amount of about 12 w/w % to about 25 w/w % of the total weight of the composition, and the biocompatible oil is propylene glycol dicaprylate/dicaprate in the amount of about 58 w/w % to about 68 w/w % of the total weight of the composition, and the cephalosporin is cefovecin sodium wherein cefovecin is in an amount of about 120 mg/mL to about 180 mg/mL. In another aspect, the ready-to-use injectable suspension composition is a sterile composition that is administered by subcutaneous injection.

In another aspect of the invention, is a ready-to-use injectable composition comprising a cephalosporin, a biocompatible oil, and a non-aqueous solvent, wherein the non-aqueous solvent is benzyl benzoate in the amount of about 18 w/w % to about 22 w/w % of the total weight of the composition, wherein the composition is a suspension for injection. In another aspect, is a ready-to-use injectable suspension composition comprising a cephalosporin, a biocompatible oil, and a non-aqueous solvent, wherein the non-aqueous solvent is benzyl benzoate in the amount of about 18 w/w % to about 22 w/w % of the total weight of the composition, and the biocompatible oil is propylene glycol dicaprylate/dicaprate in the amount of about 60 w/w % to about 65 w/w % of the total weight of the composition. In another aspect, is a ready-to-use injectable suspension composition comprising a cephalosporin, a biocompatible oil, and a non-aqueous solvent, wherein the non-aqueous solvent is benzyl benzoate in the amount of about 18 w/w % to about 22 w/w % of the total weight of the composition, and the biocompatible oil is propylene glycol dicaprylate/dicaprate in the amount of about 60 w/w % to about 65 w/w % of the total weight of the composition, and the cephalosporin is cefovecin in an amount of about 120 mg/mL to about 180 mg/mL. In another aspect, is a ready-to-use injectable suspension composition containing a cephalosporin, a biocompatible oil, and a non-aqueous solvent, wherein the non-aqueous solvent is benzyl benzoate in the amount of about 18 w/w % to about 22 w/w % of the total weight of the composition, and the biocompatible oil is propylene glycol dicaprylate/dicaprate in the amount of about 60 w/w % to about 65 w/w % of the total weight of the composition, and the cephalosporin is cefovecin in an amount of about 120 mg/mL to about 180 mg/mL. In another aspect, is a ready-to-use injectable suspension composition comprising a cephalosporin, a biocompatible oil, and a non-aqueous solvent, wherein the non-aqueous solvent is benzyl benzoate in the amount of about 18 w/w % to about 22 w/w % of the total weight of the composition, and the biocompatible oil is propylene glycol dicaprylate/dicaprate in the amount of about 60 w/w % to about 65 w/w % of the total weight of the composition, and the cephalosporin is cefovecin sodium wherein cefovecin is in an amount of about 120 mg/mL to about 180 mg/mL. In another aspect, is a ready-to-use injectable suspension composition containing a cephalosporin, a biocompatible oil, and a non-aqueous solvent, wherein the non-aqueous solvent is benzyl benzoate in the amount of about 18 w/w % to about 22 w/w % of the total weight of the composition, and the biocompatible oil is propylene glycol dicaprylate/dicaprate in the amount of about 60 w/w % to about 65 w/w % of the total weight of the composition, and the cephalosporin is cefovecin sodium wherein cefovecin is in an amount of about 120 mg/mL to about 180 mg/mL. In another aspect, is a ready-to-use injectable suspension composition comprising a cephalosporin, a biocompatible oil, and a non-aqueous solvent, wherein the non-aqueous solvent is benzyl benzoate in the amount of about 18 w/w % to about 22 w/w % of the total weight of the composition, and the biocompatible oil is propylene glycol dicaprylate/dicaprate in the amount of about 60 w/w % to about 65 w/w % of the total weight of the composition, and the cephalosporin is cefovecin sodium wherein cefovecin is in an amount of about 160 mg/mL. In another aspect, is a ready-to-use injectable suspension composition containing a cephalosporin, a biocompatible oil, and a non-aqueous solvent, wherein the non-aqueous solvent is benzyl benzoate in the amount of about 18 w/w % to about 22 w/w % of the total weight of the composition, and the biocompatible oil is propylene glycol dicaprylate/dicaprate in the amount of about 60 w/w % to about 65 w/w % of the total weight of the composition, and the cephalosporin is cefovecin sodium wherein cefovecin is in an amount of about 160 mg/mL. In another aspect, the ready-to-use injectable suspension composition is a sterile composition that is administered by subcutaneous injection.

In another aspect of the invention, is a ready-to-use injectable suspension composition comprising a cephalosporin, a biocompatible oil, and a non-aqueous solvent, wherein the non-aqueous solvent is benzyl benzoate in the amount of about 20 w/w % of the total weight of the composition, and the biocompatible oil is propylene glycol dicaprylate/dicaprate in the amount of about 61 w/w % to about 64 w/w % of the total weight of the composition, and the cephalosporin is cefovecin sodium wherein cefovecin is in an amount of about 160 mg/mL. In another aspect of the invention, is a ready-to-use injectable suspension composition containing a cephalosporin, a biocompatible oil, and a non-aqueous solvent, wherein the non-aqueous solvent is benzyl benzoate in the amount of about 20 w/w % of the total weight of the composition, and the biocompatible oil is propylene glycol dicaprylate/dicaprate in the amount of about 61 w/w % to about 64 w/w % of the total weight of the composition, and the cephalosporin is cefovecin sodium wherein cefovecin is in an amount of about 160 mg/mL. In another aspect, is a ready-to-use injectable suspension composition comprising a cephalosporin, a biocompatible oil, and a non-aqueous solvent, wherein the non-aqueous solvent is benzyl benzoate in the amount of about 20 w/w % of the total weight of the composition, and the biocompatible oil is propylene glycol dicaprylate/dicaprate in the amount of about 62 w/w % to about 63 w/w % of the total weight of the composition, and the cephalosporin is cefovecin sodium wherein cefovecin is in an amount of about 160 mg/m L. In another aspect, is a ready-to-use injectable suspension composition containing a cephalosporin, a biocompatible oil, and a non-aqueous solvent, wherein the non-aqueous solvent is benzyl benzoate in the amount of about 20 w/w % of the total weight of the composition, and the biocompatible oil is propylene glycol dicaprylate/dicaprate in the amount of about 62 w/w % to about 63 w/w % of the total weight of the composition, and the cephalosporin is cefovecin sodium wherein cefovecin is in an amount of about 160 mg/mL. In another aspect, the ready-to-use injectable suspension composition is a sterile composition that is administered by subcutaneous injection.

In another aspect of the invention, is a method of treating a bacterial infection in an animal in need thereof, by administering an effective amount of a cephalosporin in an injectable suspension composition by subcutaneous injection comprising a biocompatible oil, and a non-aqueous solvent. In another aspect, is a method of treating a bacterial infection in an animal in need thereof, by administering an effective amount of a cephalosporin in an injectable suspension composition by subcutaneous injection comprising a biocompatible oil, and a non-aqueous solvent; wherein the cephalosporin is cefovecin, the biocompatible oil is propylene glycol dicaprylate/dicaprate, and the non-aqueous solvent is benzyl benzoate. In another aspect, is a method of treating a bacterial infection in an animal in need thereof, by administering an effective amount of a cephalosporin in an injectable suspension composition by subcutaneous injection comprising a biocompatible oil, and a non-aqueous solvent; wherein the cephalosporin is cefovecin in an amount of about 150-180 mg/mL, the biocompatible oil is propylene glycol dicaprylate/dicaprate in an amount of about 58-68 w/w % of the total weight of the composition, and the non-aqueous solvent is benzyl benzoate in an amount of about 12 w/w % to about 25 w/w % of the total weight of the composition. In another aspect, is a method of treating a bacterial infection in an animal in need thereof, by administering an effective amount of a cephalosporin in an injectable suspension composition by subcutaneous injection comprising a biocompatible oil, and a non-aqueous solvent; wherein the cephalosporin is cefovecin in an amount of about 150 mg/mL to about 180 mg/mL, the biocompatible oil is propylene glycol dicaprylate/dicaprate in an amount of about 60 w/w % to about 65 w/w % of the total weight of the composition, and the non-aqueous solvent is benzyl benzoate in an amount of about 18 w/w % to about 22 w/w % of the total weight of the composition. In another aspect, is a method of treating a bacterial infection in an animal in need thereof, by administering an effective amount of a cephalosporin in an injectable suspension composition by subcutaneous injection comprising a biocompatible oil, and a non-aqueous solvent; wherein the cephalosporin is cefovecin in an amount of about 160 mg/mL, the biocompatible oil is propylene glycol dicaprylate/dicaprate in an amount of about 62 w/w % to about 63 w/w % of the total weight of the composition, and the non-aqueous solvent is benzyl benzoate in an amount of about 20 w/w % of the total weight of the composition; and wherein the composition is a sterile composition that is administered by subcutaneous injection. In another aspect, the animal is a companion animal. In another aspect, the preferred animal is canine and feline.

In another aspect of the invention, is the use of an injectable suspension composition comprising an effective amount of a cephalosporin, a biocompatible oil, and a non-aqueous solvent to prepare a medicament for treating a bacterial infection in an animal. In another aspect, is the use of an injectable suspension composition comprising an effective amount of cefovecin in an amount of about 150 mg/mL to about 180 mg/mL, a biocompatible oil that is propylene glycol dicaprylate/dicaprate in an amount of about 60 w/w % to about 65 w/w % of the total weight of the composition, and a non-aqueous solvent that is benzyl benzoate in an amount of about 18 w/w % to about 22 w/w % of the total weight of the composition to prepare a medicament for treating a bacterial infection in an animal. In another aspect of the invention, is the use of an injectable suspension composition containing an effective amount of a cephalosporin, a biocompatible oil, and a non-aqueous solvent to prepare a medicament for treating a bacterial infection in an animal. In another aspect, is the use of an injectable suspension composition comprising an effective amount of cefovecin in an amount of about 150 mg/mL to about 180 mg/mL, a biocompatible oil that is propylene glycol dicaprylate/dicaprate in an amount of about 60 w/w % to about 65 w/w % of the total weight of the composition, and a non-aqueous solvent that is benzyl benzoate in an amount of about 18 w/w % to about 22 w/w % of the total weight of the composition to prepare a medicament for treating a bacterial infection in an animal. In another aspect, is the use of an injectable suspension composition comprising an effective amount of cefovecin in an amount of about 160 mg/mL, a biocompatible oil that is propylene glycol dicaprylate/dicaprate in an amount of about 62 w/w % to about 63 w/w % of the total weight of the composition, and a non-aqueous solvent that is benzyl benzoate in an amount of about 20 w/w % of the total weight of the composition to prepare a medicament for treating a bacterial infection in an animal. In another aspect, is the use of an injectable suspension composition containing an effective amount of cefovecin in an amount of about 160 mg/mL, a biocompatible oil that is propylene glycol dicaprylate/dicaprate in an amount of about 62 w/w % to about 63 w/w % of the total weight of the composition, and a non-aqueous solvent that is benzyl benzoate in an amount of about 20 w/w % of the total weight of the composition to prepare a medicament for treating a bacterial infection in an animal; wherein the composition is a sterile composition that is administered by subcutaneous injection. In another aspect, the animal is a companion animal. In another aspect, the preferred animal is canine and feline.

DETAILED DESCRIPTION

Brief Description of Figures

FIG. 1. Viscosity versus Shear rate
FIG. 2. Viscosity vs Shear Rate with different amounts of solvent and a surfactant
FIG. 3. Viscosity versus Shear Rate with different amounts of solvent
FIG. 4. Syringe Force for Miglyol 812 and Miglyol 840
FIG. 5. Resuspension Time

DEFINITION(S)

"Animal(s)", as used herein, unless otherwise indicated, refers to an individual animal that is a mammal. Specifically, mammal refers to a vertebrate animal that is human and non-human, which are members of the taxonomic class Mammalia. Preferred animals are non-human mammals. Non-exclusive examples of non-human mammals include companion animals and livestock. Non-exclusive examples of a companion animal include: dog (canine), cat (feline), and horse (equine). The preferred companion animal is canine and feline. Non-exclusive examples of livestock include swine (pig), bovine (cow), ovine (sheep), and caprine (goat).

As used herein, percent of components of the composition for liquid components (i.e., benzyl benzoate and propylene glycol dicaprylate/dicaprate (Miglyol 840)) refers to percentages of the total weight of the composition and is referred to as "% w/w" or "w/w %" which defines the mass fraction of the compositional component expressed as a percentage, determined according to the formula $m_i/m_{tot} \times 100$, wherein $m_i$ is the mass of the substance of interest present in the composition, and $m_{tot}$ is the total mass of the composition. Further, as used herein, percent of components of the composition for solid components (i.e., cefovecin sodium) refers to percentages of the total weight of the solid component as a percent of the total compositional volume and is referred to as "% w/v" or "w/v %" which defines the mass fraction of the compositional component expressed as a percentage, determined according to the formula $m_i/m_{tot} \times 100$, wherein $m_i$ is the mass of the solid present in the composition, and $m_{tot}$ is the total volume of the composition. The density of the composition of the invention is about 1 g/mL; therefore the w/w % and w/v % values are almost equivalent.

As used herein, the term "about", refers to the indicated value of the variable and to all values of the variable that are within the experimental error of the indicated value (e.g., within the 95% confidence interval for the mean) or within 10 percent of the indicated value, whichever is greater.

Typical excipients used in injectable suspensions include, for example, flocculating and/or suspending agents, wetting agents, solvents, preservatives, antioxidants, buffering and tonicity agents. Wetting agents (e.g., glycerin, alcohols, lecithin, polysorbates, sorbitan trioleate and propylene glycol) are generally used to suspend the active ingredient in a diluent. Wetting agents tend to reduce the contact angle between the surface of the particle and the wetting agent thereby achieving maximum wetting efficiency; however, excessive amounts of the wetting agent can cause foaming and/or caking of the composition.

In some instances, flocculating agents are added to the suspension to reduce interfacial forces between particles thereby causing the formation of loose quickly settling particle aggregates (floc) that are not tightly bound and are easily redispersable. Flocculating agents including salts (e.g., NaCl, KCl, calcium salts, citrates, phosphates, and sulfates), surfactants (e.g., polyoxyethylene ethers of mixed partial fatty acid esters of sorbitol anhydrides (Tweens), the same compounds without the hydrophilic oxyethylene groups (SPANS (e.g., SPAN20)), higher molecular weight polyethylene glycols (Carbowaxes) and molecular combinations of polyoxyethylene and polyoxypropylene (Pluronics)); and hydrophilic colloids/polymers (e.g., gelatin, tragacanth and xanthan gums, cellulose derivatives (e.g., sodium carboxymethylcellulose, methyl cellulose, hydroxypropylcellulose and hydroxypropylmethylcellulose)) are generally added to the suspension to prepare a floc and to aid in resuspendability. The use of benzyl benzoate is not discussed or generally used for decreasing particle-to-particle repulsion when formulating a pharmaceutical suspension, nor is it a flocculating agent. In addition to flocculants, dispersal agents, e.g., stearic acid) can be used which reduce the particle/particle interactions that may affect electrostatic charges between particles and further aggregation and caking.

The present invention provides for a suspension formulation comprising a biocompatible oil (preferably propylene glycol dicaprylate/dicaprate (Miglyol 840)), a cephalosporin, and a non-aqueous solvent. More specifically, the present invention provides for the inclusion of benzyl benzoate as the non-aqueous solvent of choice with the cephalosporin, cefovecin sodium. The resulting suspension(s) have improved syringeability, are stable, are readily resuspended after long term storage and transportation, and are easier to use for the end user. Improved resuspendability results in an improved product because less shaking of the suspension is required before dosing and allows the product to be stored longer (i.e., longer shelf-life) without caking for a homogenous and proper dose. Inclusion of benzyl benzoate to the biocompatible oil was shown to reduce the viscosity of the suspension at high shear forces that is needed for syringeability while ensuring higher viscosity, i.e., less particle settling and caking at a low shear force to prevent caking.

In rheology, shear thinning is the non-Newtonian behavior of fluids whose viscosity decreases under shear strain, is synonymous with pseudoplastic behavior, and is usually defined as excluding time-dependent effects, such as thixotropy. Shear thinning is generally not observed in pure liquids with low molecular mass (saline), but is often seen in polymer solutions and complex fluids and suspensions. When the recovery of viscosity after disturbance is very rapid, the observed behavior is classic shear-thinning, because as soon as the shear is removed, the viscosity returns to normal. When it takes a measurable time for the viscosity to recover, thixotropic behavior is observed. Particle suspension may have a strongly non-Newtonian rheology which exerts a fundamental control on the way they flow. To ensure resuspendability and syringeability, the suspension of the invention needs to be Newtonian like, i.e., so that 1) to prevent caking, the suspension must have a high viscosity at low shear and 2) the suspension at high shear has low viscosity for syringeability. Rheological properties of an injectable suspension can provide some formidable challenges in their administration and delivery.

Viscosity describes the resistance to flow with applied stress for a particular system; a more viscous system requires greater force or stress to make it flow at the same rate as a less viscous system. An ideal suspension should exhibit a high viscosity at low shear. A fluid system will exhibit either Newtonian or non-Newtonian flow based on linear or nonlinear increase in the rate of shear with the shearing stress. The suspension viscosity can change due to concentration of active ingredient(s), particle shape, size, and distribution. In addition, the actual manufacturing process, equipment and the length and type of exposure to mixing and/or homogenization shear can have a profound effect on the final suspension product.

Sedimentation volume is a qualitative term used to describe the amount of settling that has occurred in a suspension. The sedimentation volume is defined as the ratio of the final volume, $V_u$, to the original volume, $V_0$, of the suspension. The larger the fraction, the better the suspendability. Sedimentation volume is used to evaluate the changes in suspension characteristics with time and also to compare different suspension formulations, when the ratios are plotted against time, the more horizontal the slopes, the more flocculated the suspension. Generally, the sedimentation volume is directly proportional to the size of the floc and/or particles, and the rate of settling is inversely proportional to the amount of deflocculation and/or particle-particle interactions within the diluent (medium). The sedimentation volume is the height of the sediment when compared to the height when the suspension is fully resuspended. Larger sedimentation volumes typically are associated with a suspension that resuspends better. Less packaging of the sediment occurs making it easier to resuspend (i.e., less energy needs to be put into the system via shaking). Second, the faster settling rate indicates the particles are interacting to create a flocculated system. A flocculated suspension typically resuspends better than a non-flocculated suspension. The floc that form will be larger than the original particles so they settle faster. But, because they interact with themselves and other floc they will not settle to such low sedimentation volumes. Thus, they are generally easier to resuspend. The formulation of the instant invention is a non-flocculated suspension.

Therefore, flow properties such as syringeability and injectability are necessary to evaluate and control. Syringeability describes the ability of the suspension to pass easily through a hypodermic needle on transfer from the vial prior to injection. It includes characteristics such as the ease of withdraw, clogging and foaming tendencies and accuracy of dose measurements. Increase in the viscosity, density, particle size and concentration of solids in suspension hinders the syringeability of the suspension.

Injectability refers to the performance of the suspension during injection and includes factors such as pressure or force required for injection. Evenness of flow, aspiration qualities, and freedom from clogging. The syringeability and injectability of the suspension are closely related to the viscosity and particle characteristics of the suspension, A simple ejection of the suspension into the open, if done very slowly with intermittent application of pressure to the plunger can provide certain information about the suspension. Most methods used for injectability are qualitative in nature. A force monitoring device such as an Instron can be used to determine ejection and injection pressure, and the test results can be recorded on a X-Y recorder. Another instrument to assess the injectability measures the time required to smoothly inject a solution or suspension into meat under specified pressure from a syringe through a needle. When a test solution is injected through glass and plastic syringes of various sizes, regression equations are obtained of a given syringe type and diameter using needles of various gauge. These equations permit the calculation of the expected injection time for a given syringe needle system and for a given vehicle of a certain viscosity.

Clogging or blockage of syringe needles while administrating a suspension may occur because of a single large particle or an aggregate that blocks the lumen of the needle or because of a bridging effect of the particles. It is advisable to avoid particles greater than one-third of the internal diameter of the needle to prevent clogging. Clogging, if observed at or near the needle end, is usually caused by restrictions to flow from the suspension and may involve combination of factors such as vehicle, wetting of particles, particle size, shape and distribution of particles, viscosity, and flow characteristics of the suspension.

Resuspendibility describes the ability of the suspension to uniformly disperse with minimal shaking after it has stood for some time. Qualitatively, light transmittance through the upper solution in a cylinder after it has been spun for about 2 minutes at 75 rpm can be used to detect the redispersion properties of the system. Resuspendibility becomes a problem for suspension that forms cakes on standing due to the de-flocculated particles. Caking describes a process by which the particles undergo growth and fusion to form a non-dispersible mass of material.

Variable particle size distribution in suspensions results from different factors, including preparation of suspension by precipitation methods where the degree of saturation and rate of nucleation are greatest at the beginning of the process, resulting in large particles initially and smaller particles subsequently; changes in pH caused by drug decomposition; changes in temperature; and changes during processing in several types of equipment and transfer steps, Particle size measurements are useful in that they allow aggregation or crystal growth to be evaluated. There are a number of methods used for particle size analysis; microscopic determination is preferred over Andersen pipette or subsieve sizer and turbidimetry. For particle size determination below 1 µm, photon correlation spectroscopy may be employed using a Malvern particle size analyzer.

Structured vehicles used in suspensions exhibit non-Newtonian flow and are plastic, pseudoplastic, or shear-thinning with some thixotropy. For example, sodium carboxymethycellulose (CMC) and methylcellulose (MC) methocel, most commonly used in injectable suspensions, have pseudoplastic properties. Certain grades of CMC at high levels act as pseudoplastic thixotropes. The viscosity of CMC systems is dependent upon temperature, and storage at accelerated temperature may irreversibly degrade CMC making them less useful for suspensions.

The cephalosporins are a class of β-lactam antibiotics originally derived from the fungus *Acremonium*, which was previously known as "*Cephalosporium*". Together with cephamycins, they constitute a subgroup of β-lactam antibiotics called cephems and have the general formula:

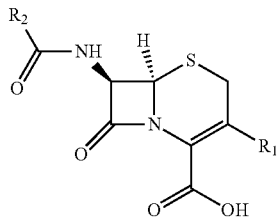

In general, changes at $R_1$ affect the microbial spectrum of activity which often affect the stability of the compound to enzymatic destruction by β-lactamases or the affinity of the compound for the drug target. Modification at $R_2$ may influence the ability of the compound to reach certain infection sites such as the central nervous system or may simply prolong the elimination half-life of the drug.

Cephalosporins have three different mechanisms of action and include: binding to specific penicillin-binding proteins, inhibition of cell wall synthesis, and activation of autolytic (self-destructive) enzymes in the bacterial cell wall. Cephalosporins are divided into five generations. However, different cephalosporins in the same generation are sometimes chemically unrelated and have different spectra of activity. A generalization taught to many health care professionals is that with subsequent generations of cephalosporins, gram-positive coverage decreases while gram-negative coverage increases.

First-generation cephalosporins are active against *Viridans* streptococci, group A hemolytic streptococci, *Staphylococcus aureus*, *E. coli*, *Klebsiella* and *Proteus* bacteria. Examples of first-generation cephalosporins include, but are not limited to, Cephalexin Cephradine, Cefadroxil, and Cefazolin, and are useful for treating bacterial infections in the skin and other soft-tissues, respiratory tract, and the urinary tract. In general, second-generation cephalosporins are more active against gram-negative organisms, making them more useful in many clinical situations. For example, second-generation cephalosporins are active against strains of *Proteus* and *Klebsiella*. Second-generation cephalosporins also combat *H. influenza*, a cause of pneumonia and sepsis. Nevertheless, first-generation cephalosporins are generally still better at treating gram-positive infections. Examples of second-generation cephalosporins include, but are not limited to, Cefoxitin, Cefotetan, Cefuroxime, and Cefprozil. Second-generation cephalosporins are generally used to treat sinusitis, otitis media, and mixed anaerobic infections including peritonitis. A major advantage of third- and fourth-generation cephalosporin antibiotics is significantly expanded coverage against gram-negative bacteria. There are several third-generation cephalosporins, including for example, Ceftriaxone, Ceftazidime, Cefovecin, Cefotaxime, Cefixime, Ceftibuten and Ceftazidime; that are useful for treating lower respiratory tract infections, skin and soft tissue infections, urinary tract infections, otitis media, bone and joint infections, and others. Cefepime is the only available fourth-generation cephalosporin in the USA while cefpirome is available in some non-USA countries. Like the third-generation cephalosporin ceftazidime, cefepime is active against *Pseudomonas aeruginosa* and can be used to treat moderate to severe pneumonia, severe urinary tract infection, and skin and soft tissue infections. Some examples of the $5^{th}$ generation cephalosporins include Ceftaroline and Ceftobiprole, that are generally reserved for serious infections thereby minimizing the risk for bacterial resistance. Overall, cephalosporins are a remarkably diverse class of antibiotics with broad bacterial coverage.

Convenia® (cefovecin sodium) is a third-generation cephalosporin with a broad-spectrum of activity against Gram-positive and Gram-negative bacteria. The action of cefovecin results from the inhibition of bacterial cell wall synthesis and is currently marketed in the USA and other countries as an antibiotic for skin wounds and abscesses in dogs and cats. The product is supplied as a lyophilized drug cake in one vial with sterile injectable water in a second vial. The packaged lyophilized drug cake (800 mg cefovecin) is reconstituted with about 10 mL sterile water for injection, i.e., 80 mg/mL cefovecin. When needed for use, the sterile water is removed from its vial by hypodermic needle and injected into the vial containing the drug cake, the drug cake is resuspended by mixing until the solids have dissolved. The solution is then withdrawn from the vial with a hypodermic needle and subsequently administered to the animal by subcutaneous injection at a dose of about 8 mg/kg body weight of the animal. In clinical studies, a single injection of Convenia® was shown to be clinically equivalent to a 14-day oral antibiotic regimen. After a single injection, therapeutic drug concentrations are maintained for approximately 7-days for *S. intermedius* infections and about 14 days for *S. canis* infections in dogs. In cats, a single injection provides therapeutic dose concentrations for about 7 days against *Pasteurella multocide* infections. The drug product provides efficacy against these bacterial strains to treat the animal skin wounds and abscesses.

Cefovecin is the non-proprietary designation for (6R,7R)-7-[[(2Z)-(2-amino-4-thiazolyl)(methoxyimino)acetyl]amino]-8-oxo-3-[(2S)-tetrahydro-2-furanyl]-5-thia-1-azabicyclo[4.2.0]oct-2-ene-2-carboxylic acid, monosodium salt (Convenia); and has the following chemical structure:

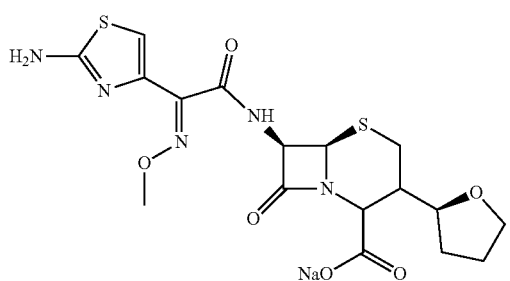

As described above, the formulation of the present invention consists of an active drug ingredient, such as a cephalosporin, and in particular, cefovecin sodium, a biocompatible oil, and a non-aqueous solvent. On a w/v %, the cefovecin is in the range of about 15-18% of the composition. The molecular weight of cefovecin is 453.49 g/mol; and the molecular weight of cefovecin sodium is 475.5 g/mol. Presuming 100% purity of the cefovecin sodium, the composition contains about 167.8 mg/mL of cefovecin sodium, accounting for about 160 mg/mL (i.e., 16 w/v %) cefovecin. Presuming 98% purity of the cefovecin sodium, the composition contains about 171.36 mg/mL cefovecin sodium, accounting for about 160 mg/mL cefovecin.

The biocompatible oil used in the present invention is composed essentially of triglycerides, which can be medium or long chain fatty acid esters of glycerol, or mixtures of triglycerides and fatty acids. Medium chain triglycerides are triglycerides with two or three fatty acids having an aliphatic tail of 6 to 12 carbon atoms. Rich sources of medium chain triglycerides include coconut oil and palm kernel oil. Long chain triglycerides are triglycerides with two or three fatty acids having an aliphatic tail of 13 to 21 carbon atoms. Rich sources of long chain triglycerides include coconut oil, palm kernel oil, peanut oil, and other vegetable oils. Trihydroxy, dihydroxy, monohydroxy or even polyhydroxy compounds may be substituted for the glycerol. The oils may be of vegetable, animal or synthetic origin. Vegetable oils include, for example, canola, corn, cottonseed, olive, peanut, sesame, soybean, safflower, coconut, sunflower, palm, and palm kernel. Mixtures of vegetable oils and medium chain triglycerides (C8-C12), and glycerin are also contemplated. Caprylic acid is a C8 medium chain triglyceride and capric acid is a C10 medium chain triglyceride. Miglyol 840 is one of these mixtures and is a propylene glycol diester of saturated plant fatty acids with chain lengths of C8 and C10. Miglyol 840 is defined herein as propylene glycol dicaprylate/dicaprate and has a molecular weight of about 709.06 g/mol. The density of Miglyol 840 at 20° C. is about 0.91-0.93 g/cm$^3$ with a viscosity of about 9-12 mPa·s. Miglyol 840 is about 65-80% caprylic acid and 20-35% capric acid. Miglyol 812 is another mixture of esters of saturated coconut and palm kernel oil derived caprylic and capric fatty acids of C8 and C10 triglycerides and glycerin. The density of Miglyol 812 at 20° C. is about 0.94-0.95 g/cm$^3$ with a viscosity of about 27-33 mPa·s. Miglyol 812 is about 50-65% caprylic acid (C8) and 30-45% capric acid (C10); and is defined as a caprylic/capric triglyceride. Even though the density of Miglyol 812 and Miglyol 840 are almost the same, the viscosity of each oil varies greatly; therefore, Miglyol 840 is a preferred biocompatible oil for the ready-to-use cephalosporin composition. The amount of the biocompatible oil ranges from about 58 w/w % to about 68 w/w % of the total weight of the composition. Preferably, the amount of the biocompatible oil ranges from about 60 w/w % to about 65 w/w % of the total weight of the composition. A more preferred amount of biocompatible oil is about 61 w/w % to about 64 w/w % of the total weight of the composition. The preferred amount is about 62 w/w % to about 63 w/w % Miglyol 840 of the total weight of the composition. The amount of Miglyol 840 added to the composition is a qs volume. The qs volume is an abbreviation for "Quantum satis", a Latin term meaning the amount which is enough, e.g., "quantity sufficient"; the amount added to bring the liquid to a final determined amount. On a weight value, the composition contains about 623 mg/mL of propylene glycol dicaprylate/dicaprate.

Solvents used in injectable suspensions can be aqueous or non-aqueous solvents. Non-aqueous solvents include water miscible and water immiscible solvents. A water miscible solvent is one that when mixed with water forms a single aqueous phase. A water immiscible solvent is one that when mixed with water forms two distinct visible layers. Choice of the solvent(s) depends on the solubility, stability and desired release characteristics of the drug. Isotonic aqueous solvents (e.g., water/saline) are typically used with non-aqueous water miscible solvents (e.g., ethanol, benzyl alcohol, glycerin, dimethylsulfoxide, propylene glycol, and the like) as co-solvents. However, their use can have undesirable side effects at the injection site and or cause myotoxicity and/or red blood cell lysis (hemolysis). An aqueous solution is a solution in which the solvent is water. Non-aqueous water-immiscible solvents used in injectable suspensions include but are not limited to: vegetable oils (e.g., sesame oil, castor oil, cotton seed oil, safflower oil, peanut oil, and the like), ethyl oleate, isopropyl myristate, and benzyl benzoate. The non-aqueous water immiscible solvents are not soluble in water, however, these solvents are miscible with each other, for example, vegetable oil and benzyl benzoate.

The concentration of the cephalosporin in the formulation of the present invention may vary between about 10 mg/mL to 250 mg/mL cefovecin. Preferably, the concentration is about 50 mg/mL to about 200 mg/mL cefovecin. A more preferred concentration of cefovecin is about 120 mg/mL to about 180 mg/mL. The most preferred concentration is about 160 mg/mL cefovecin. On a w/v %, cefovecin accounts for about 15-18% of the total volume of the composition; and more preferably, about 16-17%. If the composition is to be irradiated for sterility, then an additional 1-3% cefovecin can be added to the composition, as this is an amount that can be degraded depending on the radiation source and duration. In general, the upper concentration limit is determined when the oil composition becomes too viscous to syringe. The composition of the present invention also contains the non-aqueous solvent benzyl benzoate. The benzyl benzoate has been used as a solvent in numerous injectable formulations of cephalosporins and other drugs. Surprisingly, the use of benzyl benzoate with Miglyol 840 was shown to impart a non-caking suspension at low shear force and reasonable resuspendability and syringeability of the cefovecin sodium at high shear force. The amount of benzyl benzoate ranges from about 5 w/w % to about 30 w/w % of the total weight of the composition. A more preferred amount of benzyl benzoate is about 12 w/w % to about 25 w/w % of the total weight of the composition. A most preferred amount of benzyl benzoate is about 18 w/w % to about 22 w/w %; or about 20 w/w % of the total weight of the composition. On a weight value, the composition contains about 200 mg/mL benzyl benzoate.

Other pharmaceutically acceptable excipients normally included in such suspensions, for example, include: suspending agents, preservatives, wetting agents or flocculating agents, if desired. Suspending agents, such as gums (e.g., acacia, xanthan, carrageenan, sodium alginate and hagacanth), celluloses (e.g., sodium carboxymethylcellulose, microcrystalline cellulose, and hydroxyethylcellulose), and clays (e.g., bentonite and colloidal magnesium aluminum) may be included. Preservatives, such as methyl and propyl paraben, benzyl alcohol, chlorobutanol and thimerosal may be added. Wetting agents such as anionic (e.g., docusate sodium and sodium lauryl sulfate) and nonionic (polysorbates, polyoxamers, octoxynol-9) surfactants may be used. Thickeners, such as gelatin, natural gums and cellulose derivatives (such as those listed above as suspending agents) may be added. Buffers such as citrate and phosphate may be included as well as osmotic agents, such as sodium chloride and mannitol to control compositional pH. The composition of the present invention may be prepared by any method known in the art for the preparation of injectable suspensions. All such methods involve the active ingredient being present in a suitable solid form and suspension thereof in a liquid vehicle or diluent.

The suspension of the present invention, which contains Cefovecin sodium, as its active ingredient, is useful as an antibiotic to cure bacterial infections of animals such as companion animals and livestock. Cefovecin sodium (Convenia®) is a broad spectrum cephalosporin antibiotic active against gram-positive and gram-negative bacteria, including β-lactamase-producing strains. For dogs, Convenia® is indicated for the treatment of skin infections (secondary superficial pyoderma, abscesses, and wounds) caused by susceptible strains of *Staphylococcus intermedius* and *Streptococcus canis* (Group G). In cats, Convenia is indicated for the treatment of skin infections (wounds and abscesses) caused by susceptible strains of *Pasteurella multocida*. The effective amount of this antibiotic to be used will vary depending on the species, age and/or weight of the animal being treated. Dogs and cats are administered an 8 mg/kg subcutaneous dose.

In the present invention, the addition of benzyl benzoate to the cefovecin sodium and biocompatible oil suspension produces a suspension with high enough viscosity to prevent caking at low shear, while providing improved resuspendability at high shear and a lower viscosity for syringeability. Unlike the current cefovecin injectable lyophilized product, all that is required for the ready-to-use suspension of the present invention is resuspension. The ready-to-use suspension can more easily and readily be used without the need for separately adding a diluent from one vial to the lyophilized cake of another vial and then dissolving the product prior to injection. Therefore, there is also minimized risk of improper rehydration and needle puncture.

As previously described, surfactants are generally added to suspension formulations to promote dispersion of solids and to prevent particle caking, generally by creation of a floc. However, the ready-to-use composition of the present invention was shown that surfactants did not improve the shear thinning property of the formulation nor did the cefovecin sodium floc. In fact, formulations with surfactant did not show high viscosity at low shear rate indicating that the suspension may cake under storage conditions (FIG. 1). In addition, the presence or absence of a surfactant did not change the shear thinning behavior of the formulation that contain a shear thinning solvent (FIG. 2).

Different concentrations of benzyl benzoate were also studied to understand the impact of concentrations on viscosity. As shown in FIG. 3, the viscosity at low shear increases with increasing concentration of benzyl benzoate, while all concentrations of benzyl benzoate showed continuous reduction in viscosity as the shear rate was increased. To compare this phenomenon with a high viscosity excipient like Miglyol 812, the viscosity profile was studied in a formulation containing API suspended in 20 w/w % benzyl benzoate. As shown with the dashed-line in FIG. 3, the formulation made with Miglyol 812 showed high viscosity at low shear, but the terminal viscosity plateaued at a much higher viscosity level compared to the formulation with Miglyol 840. This was also reflected in the high syringe force needed for the formulation with Miglyol 812 (FIG. 4). Thus, the addition of benzyl benzoate, without the need for a surfactant, is sufficient to create a formulation with a favorable viscosity profile. To assess formulation resuspension, four different formulations were prepared with combinations of two different surfactants, SPAN 20 (S1) and stearic acid (S2) and two different concentrations of benzyl benzoate (6 w/w % and 20 w/w %). The resuspension time required to completely suspend the four formulations on accelerated stability at 40° C./75% RH is shown in FIG. 5. As can be observed, the formulation with 20 w/w % benzyl benzoate showed the best resuspension times after 12-weeks of storage.

We claim:

1. A ready-to-use injectable composition comprising cefovecin sodium, propylene glycol dicaprylate/dicaprate in the amount of about 58 w/w % to about 68 w/w % of the total weight of the composition and benzyl benzoate in the amount of about 12 w/w % to about 25 w/w % of the total weight of the composition, and wherein the concentration of cefovecin sodium is about 120 mg/mL to about 180 mg/mL, and wherein the composition is a suspension.

2. The ready-to-use composition of claim 1, wherein the benzyl benzoate is in the amount of about 18 w/w % to about 22 w/w % of the total weight of the composition and the propylene glycol dicaprylate/dicaprate is in the amount of about 60 w/w % to about 65 w/w % of the total weight of the composition.

3. The ready-to-use composition of claim 2, wherein the concentration of cefovecin sodium in the composition is about 160 mg/mL.

4. The ready-to-use composition of claim 3, wherein the benzyl benzoate is in the amount of about 20 w/w % of the total weight of the composition and the propylene glycol dicaprylate/dicaprate is in the amount of about 61 w/w % to about 64 w/w % of the total weight of the composition.

5. The ready-to-use composition of claim 4, wherein the propylene glycol dicaprylate/dicaprate is in the amount of about 62 w/w % to about 63 w/w % of the total weight of the composition.

6. A method of treating a bacterial infection in an animal in need thereof, by administering the ready-to-use composition of claim 1 by subcutaneous injection to the animal.

7. The method of claim 6, wherein the animal is a companion animal that is a canine animal or a feline animal.

8. The method of claim 7, wherein the propylene glycol dicaprylate/dicaprate is in the amount of about 62 w/w % to about 63 w/w % of the total weight of the composition and the benzyl benzoate is in the amount of about 20 w/w % of the total weight of the composition, and the concentration of cefovecin sodium is about 160 mg/mL.

9. A ready-to-use injectable suspension composition comprising cefovecin sodium, propylene glycol dicaprylate/dicaprate in the amount of about 60 w/w % to about 65 w/w % of the total weight of the composition and benzyl benzoate in the amount of about 18 w/w % to about 22 w/w % of the total weight of the composition, and wherein the concentration of cefovecin sodium in the composition is about 120 mg/mL to about 180 mg/mL.

10. The ready-to-use composition of claim 9, wherein the concentration of cefovecin sodium in the composition is about 160 mg/mL.

11. The ready-to-use composition of claim 10, wherein the propylene glycol dicaprylate/dicaprate is in the amount of about 61 w/w % to about 64 w/w % of the total weight of the composition.

12. The ready-to-use composition of claim 11, wherein the propylene glycol dicaprylate/dicaprate is in the amount of about 62 w/w % to about 63 w/w % of the total weight of the composition.

13. The ready-to-use composition of claim 12, wherein the benzyl benzoate is in the amount of about 20 w/w % of the total weight of the composition.

\* \* \* \* \*